(12) United States Patent
Deckelbaum et al.

(10) Patent No.: US 9,084,801 B2
(45) Date of Patent: *Jul. 21, 2015

(54) USE OF AN OMEGA-3 LIPID-BASED EMULSION FOLLOWING ISCHEMIC INJURY TO PROVIDE PROTECTION AND RECOVERY IN HUMAN ORGANS

(75) Inventors: Richard J. Deckelbaum, Hastings-on-Hudson, NY (US); Susan J. Vannucci, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/336,290

(22) Filed: Dec. 23, 2011

(65) Prior Publication Data
US 2012/0095095 A1   Apr. 19, 2012

Related U.S. Application Data

(62) Division of application No. 11/558,568, filed on Nov. 10, 2006, now abandoned.

(60) Provisional application No. 60/799,677, filed on May 12, 2006, provisional application No. 60/735,862, filed on Nov. 14, 2005.

(51) Int. Cl.
*A61K 35/60* (2006.01)
*A61K 31/202* (2006.01)
*A61K 31/22* (2006.01)

(52) U.S. Cl.
CPC .............. *A61K 35/60* (2013.01); *A61K 31/202* (2013.01); *A61K 31/22* (2013.01)

(58) Field of Classification Search
None
See application file for complete search history.

(56) References Cited

U.S. PATENT DOCUMENTS

| 4,895,876 A | 1/1990 | Schweighardt et al. |
| 5,160,759 A | 11/1992 | Nomura et al. |

(Continued)

FOREIGN PATENT DOCUMENTS

| EP | 1279400 A1 | 1/2003 |
| GB | 2388026 A | 11/2003 |

(Continued)

OTHER PUBLICATIONS

Billman et al, Prevention of Ischemia-induced Ventricular Fibrillation by Omega-3 fatty acids, 1994, Proc. Natl. Acad. Sci. USA, vol. 91, pp. 4427-4430.*

(Continued)

*Primary Examiner* — Trevor Love
(74) *Attorney, Agent, or Firm* — Evans & Molinelli PLLC; Judith A. Evans (57) ABSTRACT

The present invention provides methods of limiting cell death resulting from hypoxic-ischemia comprising, administering an omega-3 lipid-based emulsion after a hypoxic-ischemia insult. The omega-3 lipid-based emulsion preferably comprises at least 20% omega-3 oil, by weight, and wherein the omega-3 oil comprises at least 20% omega-3 triglycerides and/or diglycerides, and wherein fatty acids of the omega-3 triglyceride and/or diglycerides comprise at least 40% EPA and/or DHA. The present invention also provides novel fish-oil compositions for administration after an ischemic insult to limit cell death in the organ that underwent an ischemic event.

38 Claims, 4 Drawing Sheets

|  | Mean Damage Score |
|---|---|
| Treated Rats | 0.33 ± 0.51 |
| Control Rats | 1.83 ± 0.91 |

P-value =0.019

Rats Given 20% Fish Oil Emulsion

Control Rats (56) References Cited

U.S. PATENT DOCUMENTS

| | | | |
|---|---|---|---|
| 5,214,062 | A | 5/1993 | Mark et al. |
| 5,700,837 | A | 12/1997 | Trimbo |
| 6,020,020 | A | 2/2000 | Cain et al. |
| 6,306,908 | B1 | 10/2001 | Carlson |
| 6,448,292 | B2 | 9/2002 | Koike et al. |
| 2002/0160537 | A1 | 10/2002 | Kleinfeld |
| 2003/0144356 | A1 | 7/2003 | Goodale |
| 2003/0149118 | A1 | 8/2003 | Akashe et al. |
| 2003/0175403 | A1 | 9/2003 | Gurin |
| 2004/0247693 | A1 | 12/2004 | Carpentier et al. |
| 2007/0281993 | A1 | 12/2007 | Rozen et al. |
| 2010/0093856 | A1 | 4/2010 | Deckelbaum et al. |
| 2011/0206741 | A1 | 8/2011 | Lee et al. |
| 2012/0040934 | A1 | 2/2012 | Driscoll |

FOREIGN PATENT DOCUMENTS

| | | |
|---|---|---|
| WO | WO88/05261 A1 | 7/1988 |
| WO | 99/26620 A1 | 6/1999 |
| WO | 2004/028470 A2 | 4/2004 |
| WO | 2005/013908 A2 | 2/2005 |

OTHER PUBLICATIONS

Mooe et al, Iscemic Stroke After Acute Myocardial Infarction, 1997, Stroke, AHAJournals.org, 28, pp. 762-767 (8 pages).*

Healthnotes, Fish Oil and Cod Liver Oil, Healthnotes, Inc. Oct. 25, 2004, (wayback machine), pp. 1-6.

Chemspider, EPA, RSCI Last Accessed Mar. 18, 2011, pp. 1-2, http://www.chemspider.com/Chemical-Structure.393682.html.

Chemspider, Docosahexaenoic acid, RSCI, Last Accessed Mar. 18, 2011, pp. 1-2, http://www.chemspider.com/Chemical Structure.393183.html.

Cao, D. et al., "Chronic Administration of Ethyl Docosahexaenoate Decreases Mortality and Cerebral Edema in Ischemic Gerbils", Life Sciences (2005), vol. 78, pp. 74-81.

Fiaccadori, E. et al., "Hemodynannic, Respiratory, and Metabolic Effects of Medium-Chain Triglyceride-enriched Lipid Emulsions Following Valvular Heart Surgery", Chest (1994), vol. 106. pp. 1660-1667.

Strokin, M., et al., "Neuroprotection of rat hippocampal slices exposed to oxygen-glucose deprivation by enrichment with docosahexaenoic acid by inhibition of hydrolysis of docosahexaenoic acid-containing phospholipids by calcium independent phospholipase A2", Neuroscience (2006), vol. 140, pp. 547-553.

Williams et al., "N-3 Fatty Acid Rich Triglyceride Emulsions Are Neuroprotective after Cerebral Hypoxic-Ischemic Injury in Neonatal Mice", PLOS One, Feb. 2013, vol. 8, Issue 2, http://www.plosone.org/article/info%3Adoi%2F10.1371%2Fjournal.pone.0056233.

Hospira, Inc., "LIPOSYN II—safflower oil, soybean oil and egg phospholipids injection, emulsion", "DailyMed", Jul. 2012, pp. 1-10, Publisher: U.S. National Library of Medicine, Published in: http://dailymed.nlm.nih.gov/dailymed/drugInfo.cfm?setid=1c12b44c-f074-4a14-efad-4a6c743613cf.

ISA/US, "International Search Report and Written Opinion for the corresponding PCT application US2014/032279", Sep. 12, 2014, pp. 1-9.

Taha, Mohamed, "Buffers for the physiological pH Range: Acidic Dissociation Constants of Zwitterionic Compounds in Various Hydroorganic Media", "Annali di Chimica", 2005, pp. 105-109, vol. 95, No. 1-2, Publisher: Societa Chimica Italiana, Published in: http://onlinelibrary.wiley.com/doi/10.1002/adic.200590001/abstract.

* cited by examiner

USE OF AN OMEGA-3 LIPID-BASED EMULSION FOLLOWING ISCHEMIC INJURY TO PROVIDE PROTECTION AND RECOVERY IN HUMAN ORGANS

This application is a divisional application of U.S. patent application Ser. No. 11/558,568, filed Nov. 10, 2006 and claims priority to U.S. provisional applications 60/799,677 filed on May 12, 2006 and 60/735,862, filed on Nov. 14, 2005, the contents of all of which applications are herein incorporated by reference in their entirety.

BACKGROUND OF THE INVENTION

Cerebral hypoxia-ischemia (stroke) is a major cause of morbidity and mortality through all stages of the life cycle, including for infants born prematurely, for children in intensive care units, and for elderly with cerebral vascular accidents. Infants and children who survive hypoxic-ischemic encephalopathy demonstrate lifelong neurologic handicaps, including cerebral palsy, mental retardation, epilepsy, and learning disabilities. Vannucci, R. C. (2000) "Hypoxic-ischemic encephalopathy," *American Journal of Perinatology* 17(3): 113-120.

Cerebral hypoxia-ischemia commonly occurs in critically ill children, most notably in association with cardiopulmonary arrest. Lipid emulsions are commonly used in pediatric intensive care and are an important source of calories in these critically-ill children. Most commercially available emulsions are formed from soybean oil, which have high concentrations of omega-6 (n-6) fatty acids. Lipid emulsions rich in omega-3 (n-3) fatty acids such as α-linolenic acid, eicosapentaenoic acid (EPA), and docosahexaenoic acid (DHA) are derived from fish oils, and are not yet widely available for clinical use. However, omega-3 oils have been shown to have beneficial effects in neurologic diseases such as epilepsy, depression, and behavioral disorders. Most studies support a neuroprotective effect due to dietary administration leading to altered membrane lipid composition. In one study, intravenous α-linolenic acid given before and/or after neurologic insult was protective in two animal models, kainate-induced seizures and global ischemia via four vessel occlusion in adult Sprague-Dawley rats. Lauritzen I, Blondeau N, Heurteaux C, Widmann C, Romey G, Lazdunski M., "Polyunsaturated fatty acids are potent neuroprotectors," *The EMBO Journal*, 2000 Apr. 17; 19(8):1784-93. However, there remains a need for methods to protect the brain and other organs and tissues against damage after an initial ischemic insult. The present invention fulfills this need.

SUMMARY OF THE INVENTION

The present invention provides a method of limiting neurological damage resulting from hypoxic-ischemia comprising, administering an omega-3 lipid-based emulsion after a cerebral hypoxic-ischemia insult wherein the omega-3 lipid-based emulsion comprises omega-3 oil effective to confer protection against neurological damage.

The present invention also provides a method of limiting cell death resulting from hypoxic-ischemia comprising, administering an omega-3 lipid-based emulsion after a cerebral hypoxic-ischemia insult wherein the omega-3 lipid-based emulsion comprises omega-3 oil effective to confer protection to limit cell death.

Administration of the omega-3 lipid-based emulsion may be either enteral or parenteral. Methods of the present invention also provide further comprise administering a conventional stroke treatment or preventative medication.

Omega-3 lipid-based emulsions of the present invention comprise at least 10%, preferably at least 20%, omega-3 oil, by weight. In certain embodiments, the omega-3 oil comprises at least 10%, preferably at least 20%, omega-3 triglyceride and/or omega-3 diglyceride and the fatty acids of the omega 3-triglyceride and/or omega-3 diglyceride comprise at least 40% EPA and/or DHA.

Omega-3 lipid-based emulsions may be administered at any effective dose, such as a dose of 0.05 g/kg to 4 g/kg, and may be administered any time after a hypoxic-ischemic insult, such as 20 minutes to six hours after the ischemic insult or 0-12 hours after the ischemic insult. Additional later administrations are also contemplated, for example an additional later administration is provided 1-24 hours after the insult.

The methods of the present invention are useful when ischemia has occurred in the organs selected from the group consisting of brain, lung, heart, kidney and large or small intestine.

The present invention also provides an omega-3 lipid-based emulsion suitable for enteral or parenteral administration, wherein said emulsion confers a protective benefit on cells against cell death following a hypoxic-ischemic insult, said emulsion comprising at least 20% omega-3 oil, by weight, and wherein the omega-3 oil comprises at least 20% omega-3 triglycerides and/or diglycerides, and wherein fatty acids of the omega-3 trigylceride and/or diglycerides comprise at least 40% EPA and/or DHA.

The present invention also provides the use of an omega-3 lipid-based emulsion as described herein to make a medicament to limit neurological damage and/or cell death resulting from hypoxic-ischemic.

DETAILED DESCRIPTION OF THE INVENTION

Definitions

As used herein "omega-3 lipid-based emulsion" is an oil-in-water emulsion comprising at least about 10% omega-3 oil (and up to 100% omega-3 oil). Preferably the omega-3 lipid-based emulsion comprises at least 20% omega-3 oil.

As used herein, "omega-3 oils" means any omega-3 fatty acid, including free omega-3 fatty acids and omega-3 triglycerides and omega-3 diglycerides.

The term "omega-3 fatty acid" means a polyunsaturated fatty acid wherein one of the carbon-carbon double bonds is between the third and fourth carbon atoms from the distal end of the hydrocarbon side chain of the fatty acid. Examples of "omega-3 fatty acid" include α-linolenic acid (18:3n-3; α-ALA; $\Delta^{3,6,9}$), eicosapentaenoic acid (20:5n-3; EPA; $\Delta^{5,8,11,14,17}$), docosahexaenoic acid (22:6n-3; DHA) and docosapentaenoic acid (22:5n-3; DPA; $\Delta^{7,10,13,16,19}$), wherein EPA and DHA are most preferred. Omega-3 fatty acids having at least 20 carbon atoms are herein called "long chain omega-3 fatty acids."

The term "omega-3 triglyceride" or "omega-3 diglyceride" refers to a triglyceride or a diglyceride, respectively, comprising at least one omega-3 fatty acid esterified with a glycerol moiety. As used herein, the term "omega-3 tri/diglyceride" means that omega-3 fatty acid comprises an omega-3 triglyceride and/or a diglyceride or any combination thereof.

It is now well-established that cerebral hypoxia-ischemia of sufficient duration to deplete high energy reserves in neural cells initiates a cascade of events over the hours to days of reperfusion that culminates in extensive death, both necrotic and apoptotic. These events include the generation of reactive oxygen species and oxidative damage to cells, release of inflammatory mediators and initiation of prolonged inflammatory reactions, and ongoing apoptosis that can continue for weeks to months. This applies to ischemic injury to organs in young, adult and elderly humans.

As an example, neuronal loss following hypoxialischemia is believed to result, at least in part, from elevated glutamate release and excitoxicity. Excess glutamate activation of N-methyl-D-aspartic acid (NMDA) receptors induces pro-apoptotic pathways and inhibits anti-apoptotic signaling pathways. Omega-3 fatty acids can modify a number of signaling pathways to effect transcriptional regulation. Not being bound by theory, since prior studies by the present inventors have shown that brain fatty acid profiles are not modified following administration of omega-3 triglyceride emulsions, it is believed that the omega-3 fatty acids protect neurons by modulating signaling pathways that counter the effects of hyper stimulated NMDA receptors, protection against free radical generation and consequent oxidative damage, and thereby prevent/reduce post-ischemic inflammation and release of inflammatory mediators.

Recent evidence also indicates that routes for blood clearance and tissue uptake of fish oil omega triglycerides are very different from those of omega-6 soy oil long chain triaglycerols (LCT). For example, removal of omega-3 very long chain triaglycerol (VLCT) emulsions from blood seems to depend far less on intravascular lipolysis than does LCT emulsions. While substantial amounts of both emulsions are delivered to tissues as intact triglyceride, this pathway is likely more important for omega-3 triglyceride particles. Omega-3 triglyceride particles, VLCT, are less dependent on "classical" lipoprotein receptor related clearance pathways, than are LCT. Fatty acid derived from omega-3 triglyceride appear to act as stronger inhibitors than LCT in sterol regulatory element (SRE) dependent gene expression-genes that are involved in both triglyceride and cholesterol synthesis.

The present invention provides methods of limiting or preventing cell death and cell/tissue damage resulting from hypoxic-ischemia. "Limiting" as used herein includes decreasing and/or preventing. The methods of present invention comprise administering an omega-3 lipid-based emulsion of the present invention after an hypoxic-ischemia insult. The present invention also provides, in those cases where the hypoxic-ischemic insult can be predicted, methods of limiting or preventing cell death and cell/tissue damage comprising administering an omega-3 lipid-based emulsion of the present invention before the hypoxic-ischemia insult.

When the hypoxic-ischemic insult is cerebral, the present invention limits neural cell death and/or limits neurological damage. Since the basic mechanisms of cell death following ischemia after an hypoxic-ischemic insult are similar in most bodily organs, the present invention also provides limiting cell death in other organs such as the heart, large and small intestines, kidney and lung following an hypoxic-ischemia insult. For example, after a colonic ischemic event due to acute mesenteric artery ischemia, chronic mesenteric artery ischemia or ischemia due to mesenteric venous thrombosis, the present invention provides a method of limiting intestinal cell death. Similar prevention of cell death would apply to myocardial infarction.

Prior studies have shown that omega-6 fatty acids such as omega-6 linoleic acids are far less effective in neuroprotection and cardiac protection when provided before an ischemic event. The studies involved the administration of Intralipid®, a soy oil based emulsion containing 55% of its fatty acids as omega-6 linoleic acid, with a very low content of EPA and DHA (~2%). Further, direct injection of free fatty acids, as compared to triglycerides or diglycerides, can have serious side effects, such as encephalopathy.

Accordingly, the methods of the present invention comprise administering an omega-3 lipid-based emulsion comprising at least 10%, preferably at least 20% (up to 100%) by weight of omega-3 oil. Preferably the omega-3 oil comprises at least 10%, preferably at least 20% (up to 100%) omega-3 tri/diglycerides. The fatty acids in the omega-3 tri/diglycerides preferably comprise at least 40% (up to 100%) EPA and/or DHA.

Sources of omega-3 fatty acids may be from any suitable source such as from fish oils, other oils or may even be synthesized. Although EPA and DHA are preferred omega-3 fatty acids, other omega-3 fatty acids may be used.

Methods of the present invention preferably comprise administering omega-3 lipid-based emulsions of the present invention either enterally (for example, orogastric or nasogastric) or parenterally (for example, subcutaneous, intravenous, intramuscular, intraperitoneal). Most preferably the emulsion is administered intravenously.

Omega-3 lipid-based emulsions of the present invention are preferably provided at a dose capable of providing a protective benefit. Those skilled in the art would be able to determine the appropriate dose based on the experimental data presented herein. However, for example a suitable effective and tolerable dose for a human would be about 0.05 g/kg to about 4.0 g/kg. Higher doses may be given as necessary.

Omega-3 lipid-based emulsions of the present invention are preferably administered parenterally and/or enterally after the ischemic insult (or in some embodiments, before the insult when it can be predicted). The emulsion may be administered to prevent/reduce tissue damage after cerebral hypoxia or stroke as well as hypoxic-ischemic insults in other organs such as heart, kidney, lung, etc. Preferably an omega-3 lipid-based emulsion is administered as soon as possible after the insult (or before in cases where the insult can be predicted) to provide a greater limitation of cell death. For example, in a preferred embodiment an omega-3 lipid-based emulsion is administered from 0-12 hours after the insult. Ideally the administration occurs anywhere from 20 minutes to 6 hours after the insult. Most preferably the emulsion is administered 0-2 hours after the insult. The present invention also provides for multiple administrations of the omega-3 lipid-based emulsion. For example, the emulsion may be first administered within 20 minutes of the insult, followed by a second administration 1-24 hours after the insult. The present invention also contemplates multiple administration(s) of omega-3 lipid-based emulsions following the insult.

In another embodiment of the invention, methods of limiting or preventing cell death and cell/tissue damage resulting from hypoxic-ischemia further comprise administering an omega-3 lipid-based emulsion of the present in conjunction with standard available therapies (such as surgery and angioplasty) and/or medications given to prevent or treat hypoxia-ischemia. For example, the following drugs are often administered to prevent or treat strokes: antiplatelet medications such as aspirin, clopidogrel, dipyridamole, ticlopidine; anticoagulants such as heparin and warfarin; and thrombolytic agents such as tissue plasminogen activator.

Preparation of lipid-based emulsions suitable for intravenous delivery are known in the art. Omega-3 lipid-based emulsions according to the invention may be oil-in-water (o/w) emulsions in which the outer continuous phase consists of distilled water purified or sterilized for parenteral purposes, Such oil-in-water emulsions may be obtained by standard methods, i.e. by mixing the oil components followed by emulsification and sterilization. The pH value of the lipid emulsion may be adjusted to a physiologically acceptable value, preferably to a pH of from about 6.0 to about 9.0, more preferably from about 6.5 to about 8.5. Auxiliary agents and additives may be added to the oil mixture prior to emulsification or prior to sterilization.

Omega-3 lipid-based emulsions according to the invention can be prepared by known standard procedures with inertization. Typically, first the lipids, emulsifier and other auxiliary agents and additives are mixed and then filled up with water with dispersing. The water may optionally contain additional water-soluble components (e.g. glycerol). Preferably omega-3 lipid-based emulsions of the present invention contain lipid particles having a diameter of about 100-400 nanometer, with an average size of 300 nanometers.

The present invention also provides omega-3 lipid-based emulsions suitable for enteral or parenteral administration to provide a protective benefit on cells against cell death following a hypoxic-ischemic insult. Omega-3 lipid-based emulsions of the present invention comprise at least 10%, preferably at least 20% (up to 100%) by weight of omega-3 oil. Preferably the omega-3 oil comprises at least 10%, preferably at least 20% (up to 100%) omega-3 tri/diglyceride. Fatty acids in the omega-3 tri/diglyceride preferably comprise at least 40% (up to 100%) EPA and/or DHA. The omega-3 lipid-based emulsion preferably comprises 10% to 100% omega-3 tri/diglyceride. In a preferred embodiment, the omega-3 tri/diglyceride contains at least 40% (up to 100%) of their fatty acids as EPA and/or DHA. Preferably, omega-3 emulsions of the present invention are sterile and have a particle size that is preferably between 100-400 nanometer mean diameter, with an average size of 300 nm.

EXAMPLES

Example 1

60 Minutes of Hypoxia-Ischemia

Postnatal day 19-21 Wistar rats of both genders were subjected to unilateral (right) carotid artery ligation. See Rice, J. E., 3rd, R. C. Vannucci, et al. (1981), "The influence of immaturity on hypoxic-ischemic brain damage in the rat," *Ann Neurol* 9(2): 131-41 and Vannucci, S. J., L. B. Seaman, et al. (1996), "Effects of hypoxia-ischemia on GLUT1 and GLUT5 glucose transporters in immature rat brain," *Journal of Cerebral Blood Flow & Metabolism* 16(1): 77-81.

Figure 1:
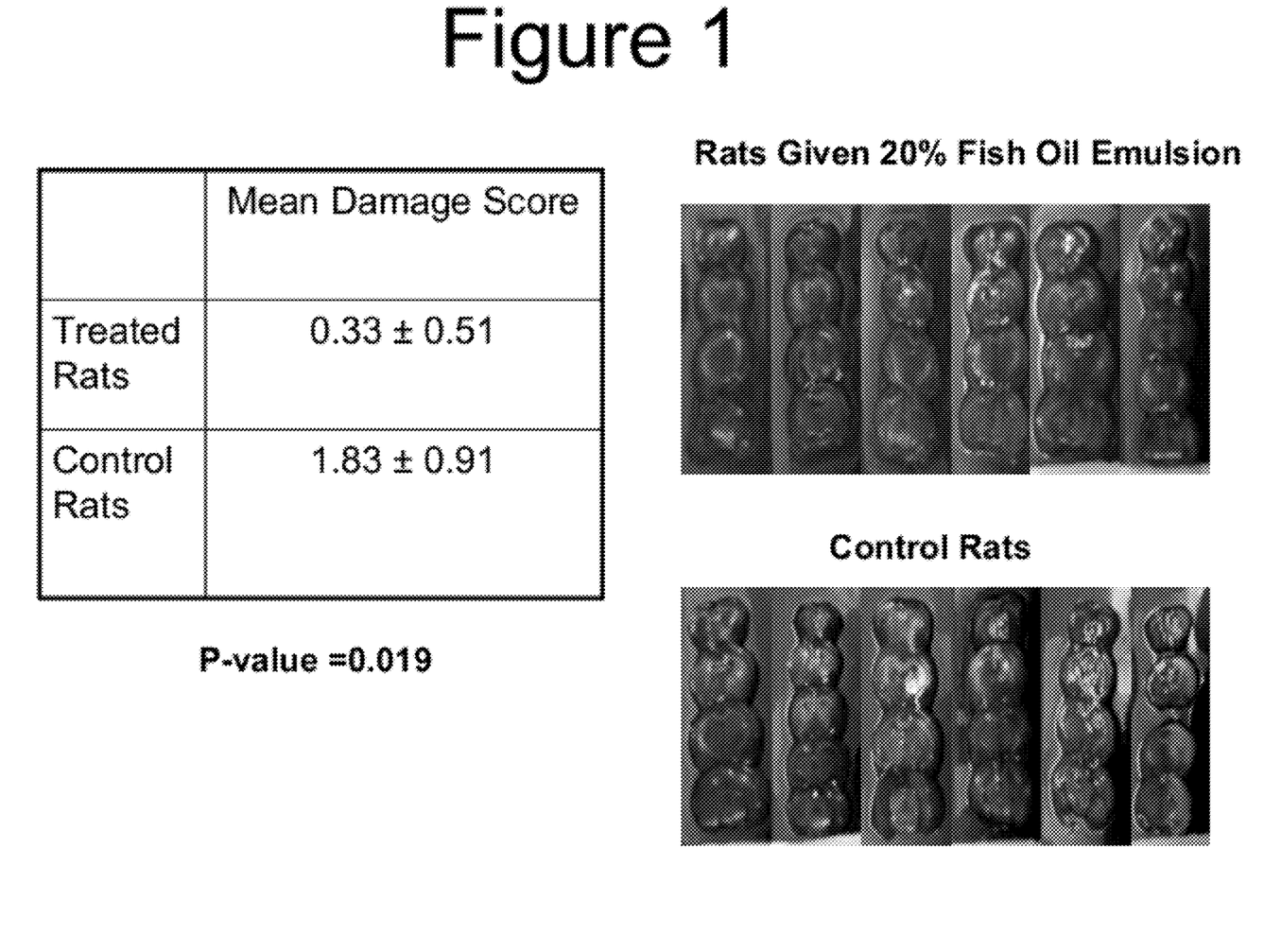
FIG. 1 provides the results of an experiment where rats were given an omega-3 lipid-based emulsion as a neuroprotective both prior and after 60 minutes of hypoxic-ischemia.

Immediately after ligation, six rats were given 50 mg 20% omega-3 lipid-based emulsion (0.25 cc)(a 20% long chain omega-3 triglyceride-based formula having >45% of total omega-3 fatty acid as eicosapentaenoic acid (EPA) and docosahexaenoic acid (DHA)) via orogastric feeding tube, and six control rats were given 0.25 cc water, both enterally. The 20% omega-3 lipid-based emulsion was made placing 20 gm of omega-3 triglyceride in 100 ml of water, and emulsifying with 1.2 gm of egg yolk lecithin. Rats were allowed to recover for 2 hours, then they underwent hypoxia-ischemia for 60 minutes of 8% oxygen at a constant temperature. The six pre-treated rats were given another dose of 50 mg omega-3 lipid-based emulsion immediately after the hypoxia-ischemia and control rats were given another 0.25 cc water. All rats were euthanized at 72 hours of reperfusion. The brains were removed and cut into 2 mm sections and stained with 2,3,5, Triphenyl-2H-tetrazolium chloride (TTC). TTC is a vital die that stains cells red that have respiring mitochondria. Dead tissue (infarct) appears white. The sections were scored as follows:

0—no evidence of edema or cell death
1—edema without cell death
2—edema with minimal cell death
3—edema with significant cell death All rats survived 60 minutes of hypoxia-ischemia. Six of the six control rats had edema and/or cell death with a mean score of 2 +/−0.83 (standard deviation), while two of the six treated rats had damage with a mean score of 0.42+/−0.62 ($p<0.005$). See FIG. 1.

Example 2

65 Minutes of Hyopoxia-Ischemia

Figure 2:
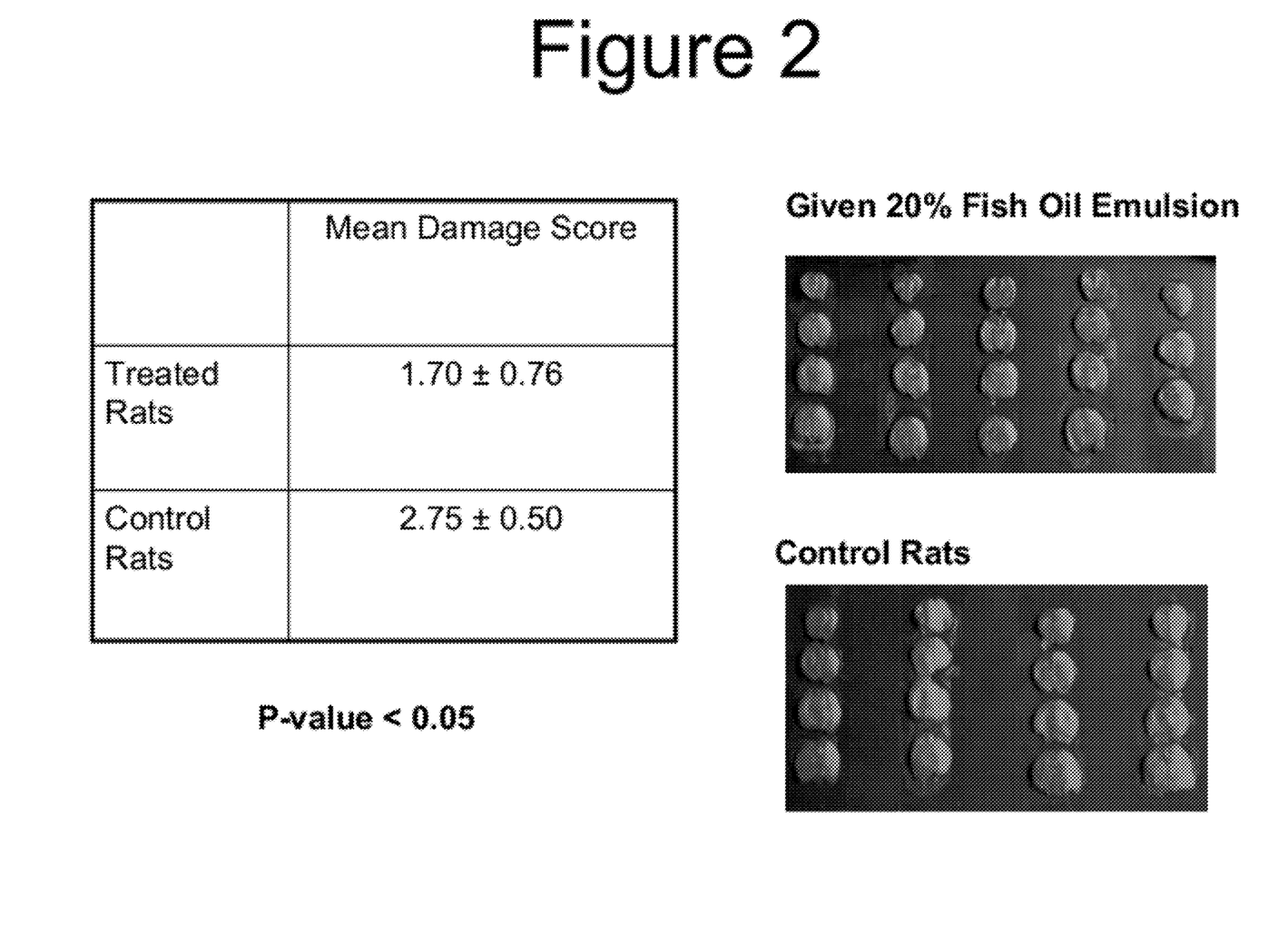
FIG. 2 provides the results of an experiment where rats were given an omega-3 lipid-based emulsion as a neuroprotective both prior and after 65 minutes of hypoxic-ischemia.

Postnatal day 19-21 Wistar rats of both genders were subjected to unilateral (right) carotid artery ligation. Immediately after ligation, six rats were given 50 mg 20% omega-3 lipid-based emulsion (0.25 cc)(20% omega-3 fatty acid based formula having ≥40% of total omega-3 fatty acid as EPA and DHA)) via orogastric feeding tube and six control rats were given 0.25 cc water, both enterally. The emulsion was made as described in Example 1. The rats recovered for two hours, and then underwent hypoxia-ischemia for 65 minutes of 8% oxygen at a constant temperature. The six pre-treated rats were given another dose of 50 mg omega-3 lipid-based emulsion immediately after the hypoxia-ischemia and control rats were given another 0.25 cc water. All rats were euthanized at 72 hours of reperfusion. The brains were removed and cut into 2 mm sections and stained with 2,3,5, Triphenyl-2H-tetrazolium chloride (TTC). The sections were scored as follows:

0—no evidence of edema or cell death
1—edema without cell death
2—edema with minimal cell death
3—edema with significant cell death The 65 minutes of hypoxia-ischemia produced damage in all rats. Four of the six control rats survived with a mean score of 2.75+/−0.50, while five of the six treated rats survived with a mean score of 1.70+1=0.76 ($p<0.05$). See FIG. 2.

Example 3

Figure 3:
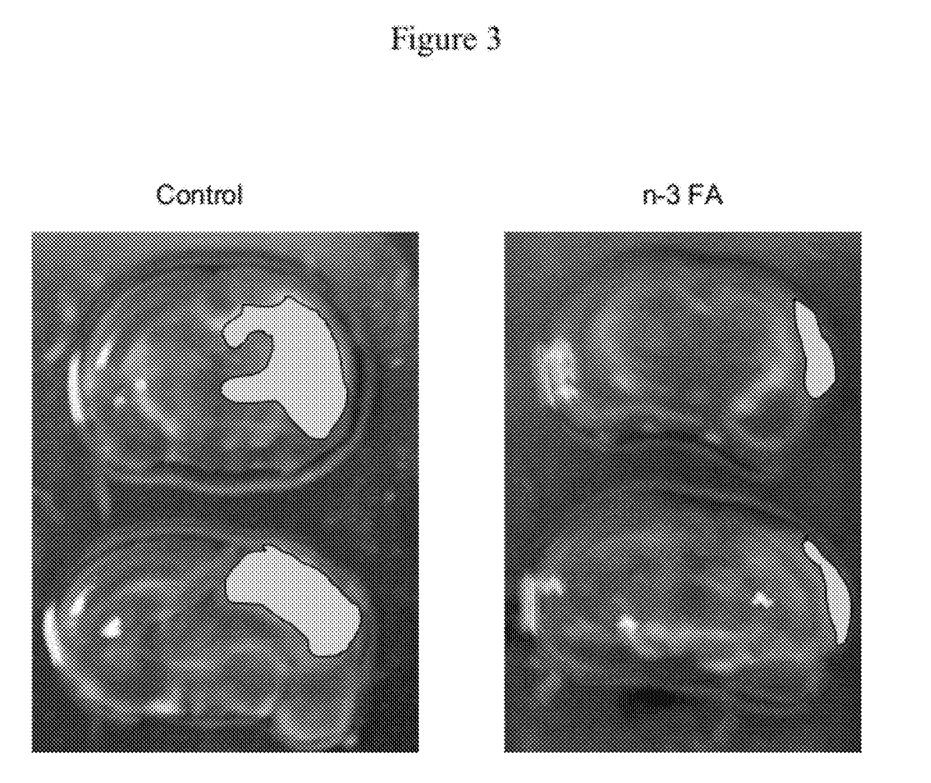
FIG. 3 shows the neuroprotective effect of omega-3 triglycerides just before hypoxic/ischemic insult on the size of brain infarcts as determined by TTC staining.

Treatment of Rats with Omega-3 Triglyceride Lipid Emulsion Prior to 60 Minutes of Hypoxia Postnatal day 19-21 Wistar rats were subjected to unilateral (right) carotid artery. Immediately after ligation, six rats were given 50 mg of a 20% omega-3 lipid-based emulsion (0.25 cc), and six control rats were given 0.25 cc water, both enterally. The emulsion was as described above in Example 1. Rats were allowed to recover for two hours, then underwent hypoxia-ischemia for 60 minutes of 8% oxygen at a constant temperature. The six pre-treated rats were given another dose of 50 mg omega-3 triglyceride lipid emulsion immediately after the hypoxia/ischemia and control rats were given another 0.25 cc water. At 72 hours of reperfusion, the rats were euthanized and their brains removed, cut into 2 mm sections and stained with 2,3,5 triphenyl-2H-tetrazolium chloride (TTC). The damage in each animal was then given a score from 0 (no damage) to 4 (>60% ipsilateral hemisphere infarcted). All of the vehicle-treated animals suffered brain damage, with a mean damage score of 2.00+0.89; the omega-3 triglyceride lipid emulsion-treated rats were significantly less damaged, having a mean damage score 0.33+0.52, p<0.05. See FIG. 3 showing the effect of administration of omega-3 triglycerides just before hypoxic-ischemic insult on the size of brain infarcts (as determined by TTC staining). Coronal sections were shown of tracings of infarcted area from anterior (top) and midsections (bottom) of brain in representative control and omega triglyceride treated rats.

These results show that when omega -3 triglycerides were administered either immediately before and/or after hypoxia-ischemia they confer a significant neuroprotection. Very similar results were obtained when the omega-3 triglycerides were injected parenterally.

Example 4

Treatment Following Hypoxic Ischemia

Post-natal day 19-21 rat pups were subjected to unilateral carotid artery ligation and 60 minutes of hypoxic ischemia, according to the previously described protocol. On four separate occasions, rats were treated by parenteral injection of omega-3 lipid-based emulsion (100 mg) immediately after the insult, and again at four hours after the insult. The emulsion was as described above in Example 1. Brain damage was evaluated by TTC staining at 72 hours of reperfusion. In each instance, administration of the omega-3 lipid-based oil emulsion provided greater than 50% protection, i.e. reduction of tissue damage.

Figure 4:
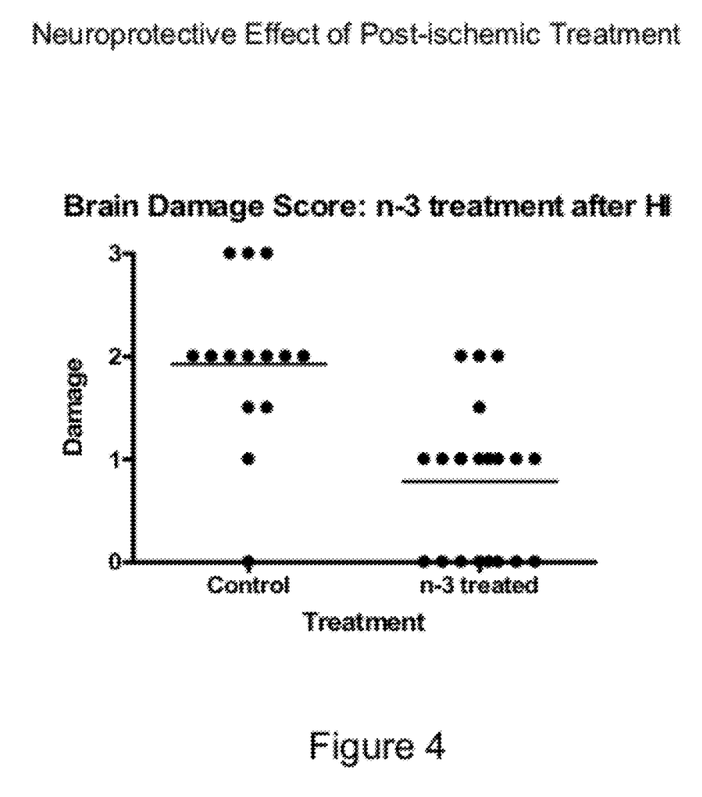
FIG. 4 shows the results of four separate experiments where rats were given an omega-3 lipid-based emulsion after 60 minutes of hypoxic-ischemia. Note that 40% of the treated animals had no brain damage and another 40% had less damage than the mean of control animals as assessed by TTC staining.

FIG. 4 shows the results of these experiments. FIG. 4 represents at total of 14 control subjects (saline-treated) and 21 treated subjects (omega-3 lipid-based emulsion treated). Mean damage scores were: 1.93±0.22 (SEM), control, 0.78±0.16 emulsion-treated; p<0.0001 by two-tailed test. The data in FIG. 4 is presented as a scatter plot. Thus, in addition to the significance of the overall protection, it can be seen that 40% of the treated animals were 100% protected (no damage at all, compared to 1/14 untreated; 40% suffered only mild damage, compared to 1/14 mildly damaged untreated animals. These results indicate that treatment following hypoxic-ischemia provides a neuroprotective benefit as indicated by a reduction of tissue damage.

Preliminary experiments conducted in the adult mouse show a comparable level of neuroprotection from hypoxic-ischemic damage.

Fatty acyl composition analyses of brain lipids (by gas liquid chromatography) after hypoxia/ischemia show no relative differences between infarcted brain versus non infarcted brain indicating that effects of acute administration of n-3 emulsions are not dependent on fatty acid compositional changes in brain membranes. In the infarcted areas, however, absolute concentrations of all fatty acids fell to similar degrees by about 15% (ug fatty acid per gram wet brain) indicating brain edema. This decrease did not occur with administration of n-3 emulsions indicating that these n-3 fatty acids prevented the brain edema as well as infarction.

Example 5

Quantification of Effects of Omega-3 Triglyceride Treatment on Cellular Targets

Studies on the effects of omega-3 triglyceride treatment on the generation of reactive oxygen species (ROS) and markers of oxidative damage, as well as indices of inflammation at 2, 4, 8 and 24 h after the hypoxic/ischemic insult are performed. Lasting protection is confirmed by brain histopathology at eight weeks following the original hypoxia-ischemic. Sections of the brain are stained (including both involved and non-involved hemispheres) with antibodies recognizing activated proteins known to participate in neuronal apoptosis (caspase 3, Jun N-terminal kinases), neuronal survival (activated Akt, phosphorylated BAD, FKHR) or to mediate the effects of NMDA-R signaling (CAM KII, and protein kinase C isoforms, in particular PKCγ and PKCζ). Sections are co-stained with antibodies recognizing neuronal specific proteins (Tau), astrocytes (GFAP) or microglia. These analyses allow quantification of the effect of omega-3 triglycerides on hypoxia-ischemia induced changes in apoptotic versus anti-apoptotic signaling in neurons, as well as gain indices of astrocytic or microglia involvement. Further, whole brain extracts from involved and non-involved hemispheres are prepared to quantify the extent of caspase, JNK and Akt activation by immunoblotting. These extracts are also used to address the question of whether omega-3 triglycerides treatment effects the activation of brain sterol regulatory element binding proteins (SREBP) in vivo.

The invention claimed is:

1. A method comprising:
1) identifying a subject who has had a hypoxic-ischemic insult,
2) administering to the subject after the hypoxic-ischemia insult a therapeutically effective amount of an omega-3 lipid-based-oil-in-water emulsion to reduce hypoxia-ischemia-induced cell and tissue damage, wherein
   (a) the oil phase of the emulsion consists essentially of omega-3 fish oil or synthetic omega-3 oil or a combination thereof and the emulsion comprises at least about 10% omega-3 oil by weight in grams per 100 ml of emulsion,
   (b) the omega-3 oil comprises at least about 10% to about 20% omega-3 triglyceride by weight per total weight of the omega-3 oil,
   (c) the fatty acid of the omega-3 triglyceride comprises at leak about 40% EPA, DHA, or a combination thereof, and
   (d) the mean diameter of lipid droplets in the emulsion is from about 100 to 400 nanometers.

2. A method comprising:
1) identifying a subject who has had a hypoxic-ischemic insult,
2) parenterally administering to the subject after the hypoxic-ischemia insult a therapeutically effective amount of an omega-3 lipid-based-oil-in-water emulsion to reduce hypoxia-ischemia-induced cell and tissue damage, wherein
   (a) the oil phase of the emulsion consists essentially of omega-3 fish oil or synthetic omega-3 oil or a combination thereof, and the emulsion comprises at least about 10% omega-3 oil by weight in grams per 100 ml of emulsion, (b) the omega-3 oil comprises at least about 10% omega-3 triglyceride by weight per total weight of the omega-3 oil,
(c) the fatty acid of the omega-3 triglyceride comprises at least about 40% EPA, DHA, or a combination thereof, and
(d) the mean diameter of lipid droplets in the emulsion is from about 100 to 400 nanometers.

3. The method of claim 1 wherein the administration is parenteral or enteral.

4. The method of claim 1 or claim 2, wherein the omega-3 lipid-based emulsion comprises at least 20% omega-3 oil by weight in grams per 100 ml of emulsion.

5. The method of claim 1 or claim 2, wherein the omega 3-triglyceride comprises about 40% EPA and/or DBA fatty acids.

6. The method of claim 2, wherein the omega-3 lipid-based emulsion comprises at least 20% omega-3 oil, by weight in grams per 100ml of emulsion, and wherein the omega-3 oil comprises at least 20% omega-3 triglyceride, and wherein the omega-3 triglyceride comprises at least 40% EPA and/or DHA fatty acids.

7. The method of claim 6 wherein the omega-3 lipid-based emulsion is administered at a dose of 0.05 g/kg to 4 g/kg.

8. The method of claim 1 or claim 2, wherein the omega-3 lipid-based emulsion is administered at 20 minutes to six hours after the hypoxic-ischemic insult.

9. The method of claim 1 or claim 2, wherein the omega-3 lipid-based based formula is administered is 0-12 hours after the hypoxic-ischemic insult.

10. The method of claim 1 or claim 2, wherein the administration is followed by a later administration of the omega-3 lipid-based emulsion.

11. The method of claim 10 wherein the later administration is provided 1-24 hours after the hypoxic-ischemic insult.

12. The method of claim 11 wherein the later administration is provided 4 hours after the hypoxic-ischemic insult.

13. The method of claim 1, wherein the omega-3 lipid-based emulsion comprises at least 20% omega-3 oil, by weight, and wherein the omega-3 oil comprises about 20% omega-3 triglyceride, and wherein the omega-3 triglyceride comprises at least 40% EPA and/or DHA fatty acids.

14. The method of claim 1 or claim 2, wherein the emulsion is administered by injection.

15. The method of claim 1 or claim 2, wherein hypoxia-ischemia insult occurs in an organ selected from the group consisting of brain, heart, kidney, large or small intestine, and lung.

16. A method of reducing inflammation or edema or neurologic damage resulting from a cerebral hypoxic-ischemic insult, comprising administering to a patient in need of such treatment a therapeutically effective amount of an omega-3 lipid-based-oil-in-water emulsion, wherein
(a) the oil phase of the emulsion consists essentially of omega-3 fish oil or synthetic omega-3 oil or a combination thereof, and the emulsion comprises at least about 10% omega-3 oil by weight in grams per 100 ml of emulsion,
(b) the omega-3 oil comprises at least about 10% to about 20% omega-3 triglyceride by weight per total weight of the omega-3 oil,
(c) the fatty acid of the omega-3 triglyceride comprises at least about 40% EPA, DHA, or a combination thereof, and
(d) the mean diameter of lipid droplets in the emulsion is from about 100 to 400 nanometers.

17. A method of reducing inflammation or edema or neurologic damage resulting from a cerebral hypoxic-ischemia insult, comprising parenterally administering to a patient in need of such treatment a therapeutically effective amount of an omega-3 lipid-based-oil-in-water emulsion, wherein
(a) the oil phase of the emulsion consists essentially of omega-3 fish oil or synthetic omega-3 oil or a combination thereof, and the emulsion comprises at least about 10% omega-3 oil by weight in grams per 100 ml of emulsion,
(b) the omega-3 oil comprises at least about 10% omega-3 triglyceride by weight per total weight of the omega-3 oil,
(c) the fatty acid of the omega-3 triglyceride comprises at least about 40% EPA, DHA, or a combination thereof, and
(d) the mean diameter of lipid droplets in the emulsion is from about 100 to 400 nanometers.

18. The method of claim 16 or claim 17, wherein the omega-3 oil comprises about 10% omega-3 triglyceride.

19. The method of claim 18 wherein the omega 3-triglyceride comprises about 40% EPA and/or DHA fatty acids.

20. The method of claim 17, wherein the omega-3 lipid-based emulsion comprises at least 20% omega-3 oil, by weight, and wherein the omega-3 oil comprises at least 20% omega-3 triglyceride, and wherein the omega-3 triglyceride comprise at least 40% EPA and/or DHA fatty acids.

21. The method of claim 16, wherein the omega-3 lipid-based emulsion comprises at least 20% omega-3 oil, by weight, and wherein the omega-3oil comprises about 20% omega-3 triglyceride, and wherein the omega-3 triglyceride comprise at least 40% EPA and/or DHA fatty acids.

22. The method of claim 16 or claim 17, wherein the emulsion is administered by injection.

23. The method of claim 2 or claim 17, wherein the omega-3 oil is 100% omega-3 triglyceride.

24. The method of claim 1 or claim 2, wherein the hypoxia-ischemia-induced cell and tissue damage is in the heart.

25. The method of claim 24 wherein the hypoxic-ischemia insult is a result of myocardial infarction.

26. The method of claim 6 or claim 13, wherein the hypoxia-ischemia induced cell and tissue damage is in the heart.

27. The method of claim 24 wherein the emulsion is administered by injection.

28. A method of treating stroke, comprising administering to a patient in need of such treatment a therapeutically effective amount of an omega-3 lipid-based-oil-in-water emulsion, wherein
(a) the oil phase of the emulsion consists essentially of omega-3 fish oil or synthetic omega-3 oil or a combination thereof, and the emulsion comprises at least about 10% omega-3 oil by weight in grams per 100 ml of emulsion,
(b) the omega-3 oil comprises at least about 10% to about 20% omega-3 triglyceride by weight per total weight of the omega-3 oil,
(c) the fatty acid of the omega-3 triglyceride comprises at least about 40% EPA, DHA, or a combination thereof, and
(d) the mean diameter of lipid droplets in the emulsion is from about 100 to 400 nanometers.

29. A method of treating stroke comprising administering to a patient in need of such treatment comprising parenterally administering to a patient in need of such treatment, a therapeutically effective amount of an omega-3 lipid-based-oil-in-water emulsion to reduce inflammation, wherein (a) the oil phase of the emulsion consists of consists essentially of omega-3 fish oil or synthetic omega-3 oil or a combination thereof, and the emulsion comprises at least about 10% omega-3 oil by weight in grams per 100 ml of emulsion,
(b) the omega-3 oil comprises at least about 10% omega-3 triglyceride by weight per total weight of the omega-3 oil,
(c) the fatty acid of the omega-3 triglyceride comprises at least about 40% EPA, DHA, or a combination thereof, and
(d) the mean diameter of lipid droplets in the emulsion is from about 100 to 400 nanometers.

30. The method of claim 29, wherein the omega-3 lipid-based emulsion comprises at least 20% omega-3 oil, by weight, and wherein the omega-3 oil comprises at least 20% omega-3 triglyceride, and wherein the omega-3 triglyceride comprise at least 40% EPA and/or DHA fatty acids.

31. The method of claim 28, wherein the omega-3 lipid-based emulsion comprises at least 20% omega-3 oil, by weight, and wherein the omega-3 oil comprises about 20% omega-3 triglyceride, and wherein the omega-3 triglyceride comprise at least 40% EPA and/or DHA fatty acids.

32. The method of claim 28 or claim 29, wherein the emulsion is administered by injection.

33. The method of claim 29, wherein the omega-3 oil is 100% omega-3 triglyceride.

34. The method of claim 28 or claim 29, wherein the omega-3 lipid-based emulsion is administered at 20 minutes to six hours after the stroke.

35. The method of claim 1 or claim 2, wherein the hypoxia-ischemia-induced cell and tissue damage comprises cell death.

36. The method of claim 1 or claim 2, wherein the hypoxia-ischemia insult is cerebral.

37. The method of claim 36, further comprising administering a conventional stroke treatment or preventative medication.

38. The method of claim 36, wherein the hypoxia-ischemia-induced cell damage is neurologic damage.

* * * * *